United States Patent
Weisner et al.

(10) Patent No.: US 9,844,341 B2
(45) Date of Patent: Dec. 19, 2017

(54) PATIENT INTERFACE FOR REUSABLE OPTICAL SENSOR

(71) Applicant: ZOLL Medical Corporation, Chelmsford, MA (US)

(72) Inventors: Steven J. Weisner, Bedford, MA (US); Peter J. Scott, Sutton, MA (US); Gwenn Ellerby, Natick, MA (US); John Cain, Nashua, NH (US); Sean M. Frick, Nashua, NH (US); Babs R. Soller, Carlsbad, CA (US); Ulrich R. Herken, Medford, MA (US); Annemarie E. Silver, Bedford, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 2 days.

(21) Appl. No.: 14/826,861

(22) Filed: Aug. 14, 2015

(65) Prior Publication Data

US 2016/0045163 A1  Feb. 18, 2016

Related U.S. Application Data

(60) Provisional application No. 62/037,334, filed on Aug. 14, 2014.

(51) Int. Cl.
   *A61B 5/00* (2006.01)
   *A61B 5/1455* (2006.01)

(52) U.S. Cl.
   CPC ........ *A61B 5/6833* (2013.01); *A61B 5/14552* (2013.01); *A61B 2560/0443* (2013.01);
   (Continued)

(58) Field of Classification Search
   CPC .............. A61B 5/6833; A61B 5/14552; A61B 2560/0443; A61B 2562/0233; A61B 2562/046; A61B 2562/164
   See application file for complete search history.

(56) References Cited

U.S. PATENT DOCUMENTS

5,224,882 A * 7/1993 Olms ..................... A61N 1/048
                                                 439/725
6,920,345 B2   7/2005 Al-Ali et al.
(Continued)

FOREIGN PATENT DOCUMENTS

EP       0756847       2/1997
WO    WO 2013/023071   2/2013

OTHER PUBLICATIONS

Final Office Action for U.S. Appl. No. 13/570,939, dated Jan. 21, 2016.
(Continued)

*Primary Examiner* — Catherine Voorhees
(74) *Attorney, Agent, or Firm* — Wilmer Cutler Pickering Hale and Dorr LLP

(57) ABSTRACT

A disposable patient interface includes a reusable sensor that removably mounts within a shoe of the disposable patient interface when at least one protrusion on opposite ends of the sensor removably lock with corresponding at least one aperture on opposite portions of the shoe. The patient interface includes a compliant structure which conforms to a patient's body upon placement thereon without causing wrinkles in the compliant structure so as to maximize adhesion of the compliant structure against skin on the patient's body when the compliant structure is conformed to muscle underlying skin on the patient's body.

29 Claims, 8 Drawing Sheets

(52) U.S. Cl.
    CPC . *A61B 2562/0233* (2013.01); *A61B 2562/046* (2013.01); *A61B 2562/164* (2013.01)

(56) References Cited

U.S. PATENT DOCUMENTS

| | | | |
|---|---|---|---|
| 6,985,764 B2* | 1/2006 | Mason | A61B 5/14552 |
| | | | 29/846 |
| 7,460,897 B1 | 12/2008 | Flessland et al. | |
| 8,505,821 B2 | 8/2013 | Medina et al. | |
| 2005/0245797 A1* | 11/2005 | Al-Ali | A61B 5/14552 |
| | | | 600/344 |
| 2006/0074283 A1 | 4/2006 | Henderson et al. | |
| 2006/0074823 A1 | 4/2006 | Heumann et al. | |
| 2007/0244378 A1 | 10/2007 | Al-Ali et al. | |
| 2009/0024013 A1 | 1/2009 | Soller | |
| 2010/0130875 A1 | 5/2010 | Banet et al. | |
| 2011/0205535 A1 | 8/2011 | Soller et al. | |
| 2012/0123232 A1 | 5/2012 | Najarian et al. | |
| 2014/0224829 A1* | 8/2014 | Capone | F04B 49/06 |
| | | | 222/23 |
| 2015/0297137 A1 | 10/2015 | Welch et al. | |

OTHER PUBLICATIONS

International Search Report for International Application No. PCT/US2012/050167, dated Nov. 27, 2012.

Non-Final Office Action for U.S. Appl. No. 13/570,939, dated Aug. 20, 2015.

Non-Final Office Action for U.S. Appl. No. 13/570,939, dated Mar. 10, 2015.

\* cited by examiner

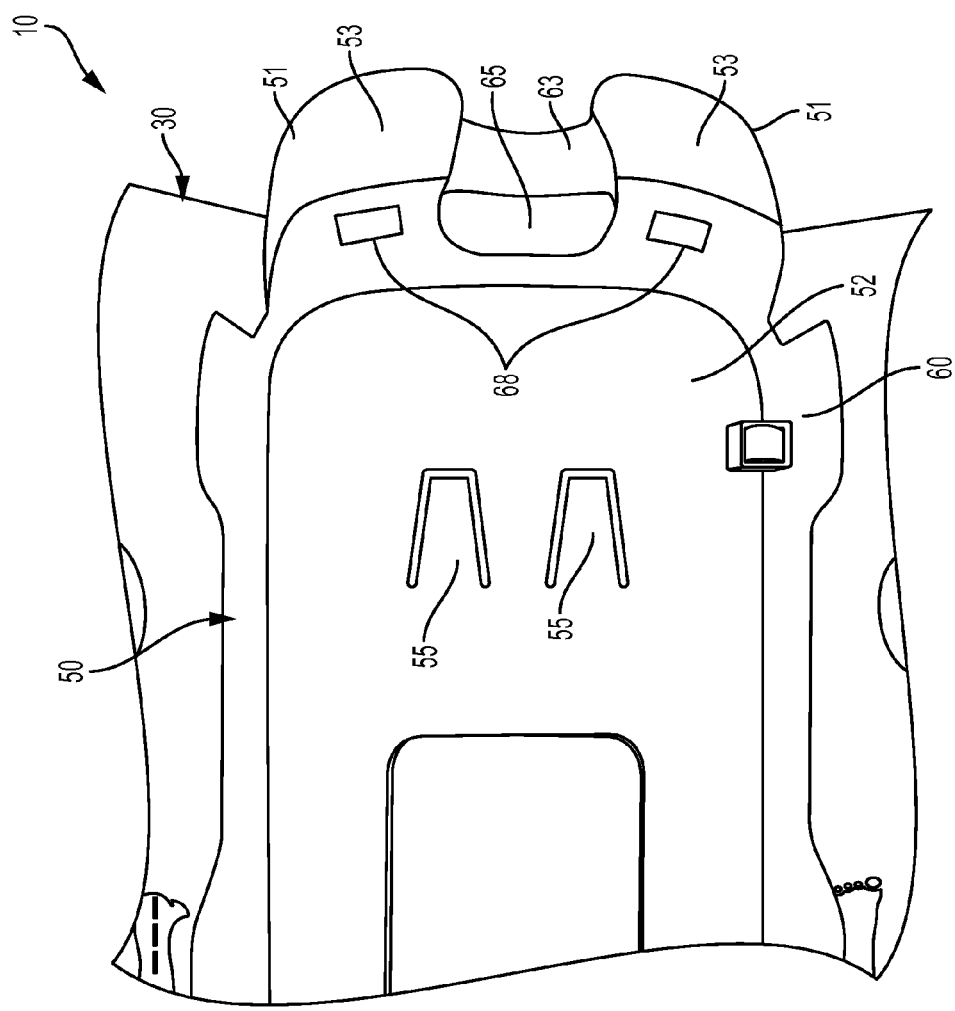

200

202

PROVIDE PATIENT INTERFACE W/ CONFORMAL PLACEMENT ELEMENT HAVING AT LEAST ONE WING W/ INSTRUCTIONAL DIAGRAM ILLUSTRATING PROPER PLACEMENT AND LOCATION OF PATIENT INTERFACE AGAINST USER'S BODY

204

PLACE PATIENT INTERFACE AGAINST PATIENT'S BODY WHILE SIMULTANEOUSLY LOOKING AT PATIENT INTERFACE AND PATIENT'S BODY UNTIL PATIENT INTERFACE IS PROPERLY PLACED

FIG. 7

PATIENT INTERFACE FOR REUSABLE OPTICAL SENSOR

CROSS-REFERENCE TO RELATED APPLICATION(S)

This application claims priority to, and the benefit of, U.S. Provisional Application 62/037,334, filed Aug. 14, 2014, for all subject matter common to both applications. The disclosure of said provisional application is hereby incorporated by reference in its entirety.

FIELD OF THE INVENTION

The present invention relates to a patient interface for a reusable optical sensor. In particular, the present invention relates to a patient interface for a reusable optical sensor that permits rapid insertion and removal of the reusable optical sensor by a user.

BACKGROUND

Disposable patient interfaces permit reuse of an optical sensor so that the sensor can be sterilized or cleaned between patients and reused after disposing the patient interface, for example, to protect against the risk of infection. Existing patient interfaces often include reusable optical sensors that are difficult to quickly insert and remove from the patient interface, for example during an emergency, due to the way in which the patient interface is mechanically coupled to the sensor.

SUMMARY

There is a need for a disposable patient interface that facilitates rapid insertion and removal of a reusable optical sensor in the disposable patient interface. The present invention is directed toward further solutions to address this need, in addition to having other desirable characteristics. Specifically, the disposable patient interface of the present invention includes a reusable sensor that removably mounts within a shoe when at least one protrusion on opposite ends of the sensor removably lock with corresponding at least one aperture on opposite portions of the shoe.

In accordance with an embodiment of the present invention, a patient interface for a reusable optical sensor is provided. The patient interface includes a conformal placement element and a shoe. The conformal placement element includes a first surface and a second surface opposite the first surface. The conformal placement element has a compliant structure which conforms to a patient's body upon placement of the first surface thereon. The shoe is fixed with the second surface of the conformal placement element removably receives a reusable optical sensor. The shoe includes a heel portion, a toe portion, a medial portion therebetween, a base positioned against the second surface of the conformal placement element from the heel portion to the toe portion, and a barrier extending around a perimeter of the base. The barrier includes a first wall portion and a second wall portion opposite to the first wall portion. The first wall portion and the second wall portion each include at least one aperture which removably locks with at least one protrusion on the reusable optical sensor. The barrier frames the reusable optical sensor when the reusable optical sensor is removably mounted in the shoe when the at least one aperture is removably locked with the at least one protrusion.

In accordance with aspects of the present invention, the compliant structure comprises a material selected from the group consisting of open celled foam, closed cell foam, natural rubber, synthetic rubber, and thermoplastic elastomer. In accordance with aspects of the present invention, the material comprises a black polyurethane foam.

In accordance with aspects of the present invention, the compliant structure conforms to a part of patient's body selected from the group consisting of a deltoid, an upper arm, a calf, a thigh, a forearm, an upper back, and a lower back. In accordance with aspects of the present invention, the compliant structure comprises a plurality of wings which collectively cause optical elements of the sensor to rest flush against the patient's body when the compliant structure conforms to the patient's body without permitting ambient air or light to pass between the optical elements and the patient's body. In accordance with aspects of the present invention, at least one of the plurality of wings comprises an instructional diagram illustrating proper placement and location of the patient interface against the patient's body. In accordance with aspects of the present invention, the diagram is disposed within the field of view of a user as they place the patient interface against the patient's body, enabling a user to properly place the patient interface against the patient's body while simultaneously looking at the patient's body until the patient interface is properly placed.

In accordance with aspects of the present invention, the plurality of wings includes a first wing proximal the toe portion, a second wing positioned proximal the medial portion on a first side of the shoe, a third wing positioned proximal the medial portion on a second side of the shoe opposite the second wing, a fourth wing positioned proximal the heel portion on the first side of the shoe, and a fifth wing positioned proximal the heel portion on the second side of the shoe opposite the fourth wing. In accordance with aspects of the present invention, the first wing secures the toe portion of the shoe in place when the first wing conforms to muscle underlying skin on the patient's body. In accordance with aspects of the present invention, first wing adheres to skin on the patient's body without causing wrinkles to form in the plurality of wings. In accordance with aspects of the present invention, the second wing and the third wing comprise a first pair of wings which are sized and dimensioned to conform to muscle underlying skin on the patient's body. In accordance with aspects of the present invention, the first pair of wings adhere to skin on the patient's body without causing wrinkles to form in the plurality of wings. In accordance with aspects of the present invention, the first pair of wings are symmetrical. In accordance with aspects of the present invention, the fourth wing and the fifth wing comprise a second pair of wings which are sized and dimensioned to secure the heel portion of the shoe in place when the second pair of wings conform to muscle underlying skin on the patient's body. In accordance with aspects of the present invention, the second pair of wings adhere to skin on the patient's body without causing wrinkles to form in the plurality of wings. In accordance with aspects of the present invention, the second pair of wings are symmetrical. In accordance with aspects of the present invention, at least one of the plurality of wings comprises a tab which is a continuation of a removable liner and extends beyond a perimeter edge of the compliant structure, enabling removal of the removable liner from the compliant structure.

In accordance with aspects of the present invention, the shoe further includes at least one actuator projecting from the barrier proximal the heel portion. When pressed the at least one actuator causes a flexing motion of the shoe, which in turn causes the at least one protrusion proximal either the first wall portion or the second wall portion to unlock from the at least one aperture removably locked with the at least one protrusion proximal either the first wall portion or the second wall portion, which in turn causes at least a portion of the reusable optical sensor proximal the heel portion to dismount from the shoe. In accordance with aspects of the present invention, the at least one actuator includes a depression which provides a visual cue for a user to press the at least one actuator. In accordance with aspects of the present invention, the at least one actuator includes two actuators coupled together by an inverted bridge which provides a gap through which a cable or case extension coupled to the reusable optical sensor can pass. Depression of at least one of the two actuators while simultaneously lifting or pulling the cable or end of the case extension enables a user to rapidly dismount the reusable optical sensor from the disposable patient interface using a single hand.

In accordance with aspects of the present invention, the shoe further includes at least one elastic spring energy storage element disposed on the base proximal the heel portion. The at least one elastic spring energy storing element stores elastic spring energy when elastically deformed into a first position co-planar with the base when the reusable optical sensor is removably mounted in the shoe. The at least one elastic spring energy storage element transfers elastic energy stored therein to the reusable optical sensor when the at least one elastic energy storage element springs to a second position angled away from the plane of the base and toward the reusable optical sensor, pushing the reusable optical sensor to be dismounted from the shoe.

In accordance with aspects of the present invention, the shoe includes an opening passing completely through the base proximal the medial portion of the shoe. The opening has a perimeter which frames optical elements proud from the reusable optical sensor. In accordance with aspects of the present invention, an optically clear window is aligned with the opening. In accordance with aspects of the present invention, the optically clear window further includes an adhesive surface along at least a portion thereof. In accordance with aspects of the present invention, the optically clear window is an optical tape. In accordance with aspects of the present invention, an adhesive layer is disposed on at least a portion of the first surface of the conformal placement element. In accordance with aspects of the present invention, the adhesive layer is a biocompatible, near-infrared transparent material. In accordance with aspects of the present invention, the adhesive layer is a transfer adhesive. In accordance with aspects of the present invention, a removable liner is positioned proximate the adhesive layer. In accordance with aspects of the present invention, at least a portion of the removable liner is sufficiently opaque to prevent a user from using the reusable optical sensor without first removing the liner. In accordance with aspects of the present invention, the reusable optical sensor includes a security sensor which prevents the reusable optical sensor from operating when the reusable optical sensor is not removably mounted in the shoe. In accordance with aspects of the present invention, the security sensor is a hall sensor including the security sensor and a magnet coupled to the base, wherein the magnet generates a magnetic field that can only be detected by the reusable optical sensor when the reusable optical sensor is removably mounted in the shoe.

In accordance with aspects of the present invention, the barrier is opaque. In accordance with aspects of the present invention, the barrier has a minimal height dimension that is equal to or greater than a minimum thickness dimension of the reusable optical sensor.

In accordance with aspects of the present invention, the at least one aperture is two apertures and the at least one protrusion is two protrusions.

In accordance with aspects of the present invention, the reusable optical sensor includes at least a portion of which is indented for receiving a magnet coupled to the base.

In accordance with an embodiment of the present invention, a method of removably mounting a reusable optical sensor in a disposable patient interface is provided. In the method, a reusable optical sensor is provided. The reusable optical sensor includes a first end proximal a cable or case extension of the sensor and a second end opposite the first end. In the method, a patient interface is also provided. The patient interface includes a conformal placement element and a shoe. The conformal placement element has a compliant structure which conforms to a patient's body upon placement thereon. The shoe is fixed with the conformal placement element and removably receives a reusable optical sensor. The shoe includes a heel portion, a toe portion, a medial portion therebetween, a base positioned against the second surface of the conformal placement element from the heel portion to the toe portion, and a barrier extending around a perimeter of the base. The barrier includes a first wall portion and a second wall portion opposite to the first wall portion. The first wall portion and the second wall portion each include at least one aperture which removably locks with at least one protrusion on the reusable optical sensor. At least one actuator projects from the barrier proximal the heel portion. The method involves sliding the second end of the sensor toward the barrier proximal the toe portion of the shoe so that the at least one protrusion proximal the second end of the reusable optical sensor removably locks with the at least one aperture proximal the toe portion of the shoe, and then pushing the first end of the reusable optical sensor toward the base proximal the heel portion of the shoe so that the at least one protrusion proximal the first end of the reusable optical sensor removably locks with the at least one aperture proximal the heel portion of the shoe, thereby removably mounting the reusable optical sensor in the disposable patient interface.

In accordance with an embodiment of the present invention, a method of dismounting a removably mounted reusable optical sensor is provided. Dismounting the removably mounted reusable optical sensor involves pressing the at least one actuator and optionally lifting a cable or end of a case extension disposed proximal the first end of the sensor away from the shoe. Pressing the at least one actuator causes a flexing motion of the shoe, which in turn causes the at least one protrusion proximal either the first wall portion or the second wall portion to unlock from the at least one aperture removably locked with the at least one protrusion proximal either the first wall portion or the second wall portion, which in turn causes at least a portion of the reusable optical sensor proximal the heel portion to dismount from the shoe. The pressing and lifting are optionally performed using a same hand of the user to dismount the sensor from the patient interface.

In accordance with an embodiment of the present invention, a method of placing a patient interface on a patient's body is provided. In the method a patient interface is provided. The patient interface includes a conformal placement element, a shoe fixed with the conformal placement element, and a reusable optical sensor removably mounted in the shoe. The compliant structure conforms to a patient's body upon placement thereon, and includes a plurality of wings, at least one of which includes an instructional diagram disposed within the field of view of a user illustrating proper placement and location of the patient interface against the patient's body. In the method, the patient interface is placed against the patient's body while simultaneously looking at the patient interface and the patient's body until the patient interface is properly placed.

BRIEF DESCRIPTION OF THE FIGURES

These and other characteristics of the present invention will be more fully understood by reference to the following detailed description in conjunction with the attached drawings, in which:

FIG. 4 is an expanded top view of the patient interface of FIG. 1, showing the heel portion of the shoe with at least one actuator for dismounting a reusable optical sensor that is removably mounted in the shoe.

FIG. 7 is a flowchart depicting a method of placing a disposable patient interface against a patient's body, in accordance with aspects of the present invention.

DETAILED DESCRIPTION

Figure 1:
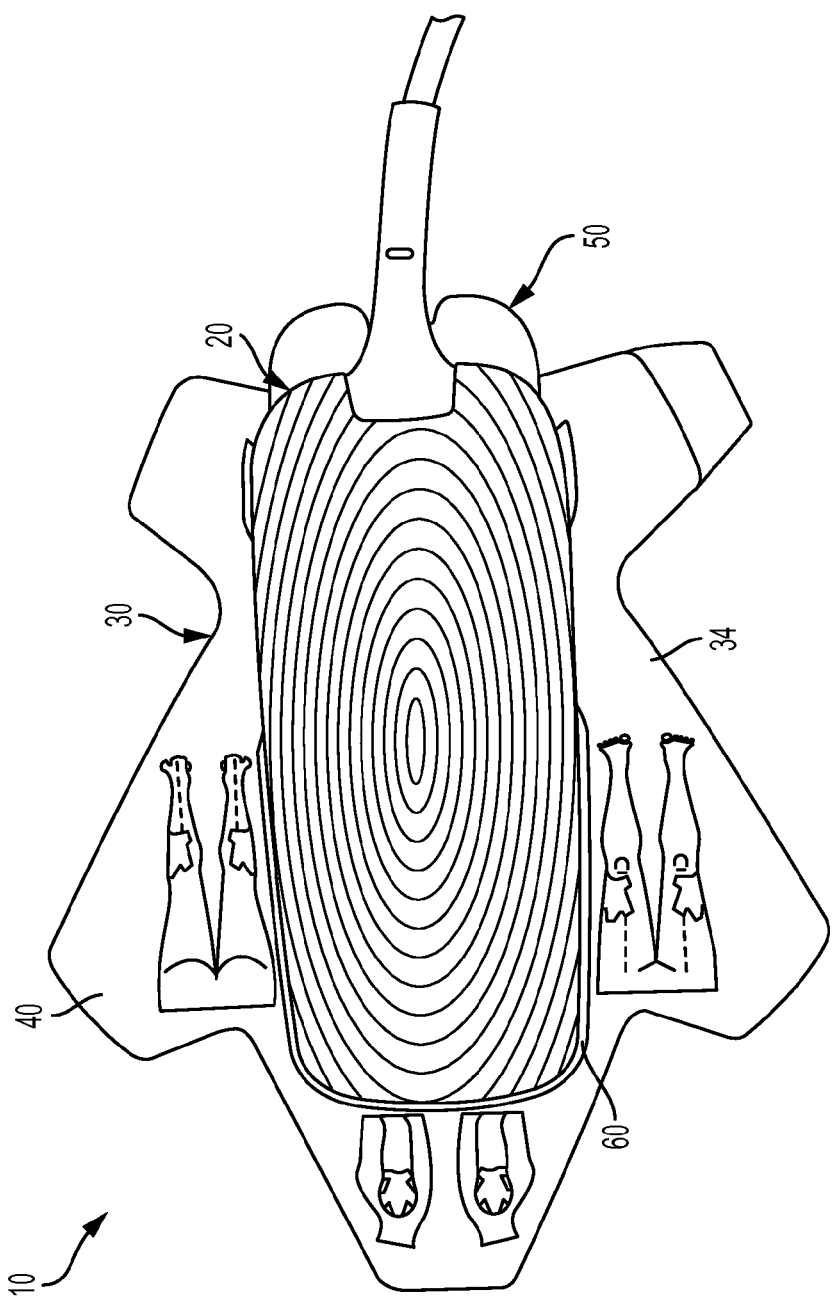
FIG. 1 is a top view of a patient interface comprising a reusable optical sensor removably mounted in a shoe, which is fixed with a conformal placement element, in accordance with an example embodiment of the present invention.

An illustrative embodiment of the present invention relates to a reusable sensor that removably mounts within a shoe of a disposable patient interface when at least one protrusion on opposite ends of the sensor removably lock with corresponding at least one aperture on opposite portions of the shoe. The patient interface includes a compliant structure that conforms to a patient's body upon placement thereon without causing wrinkles in the compliant structure so as to maximize adhesion of the compliant structure against skin on the patient's body when the compliant structure is conformed to muscle underlying skin on the patient's body.

FIGS. 1 through 7, wherein like parts are designated by like reference numerals throughout, illustrate an example embodiment or embodiments of a disposable patient interface for a reusable optical sensor that removably mounts within a shoe when at least one protrusion on opposite ends of the sensor removably locks with a corresponding at least one aperture on opposite portions of the shoe, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Referring now to FIG. 1, there is shown an example embodiment of a patient interface 10 for a reusable optical sensor 20 that includes a conformal placement element 30 and a shoe 50 with the reusable optical sensor 20 removably mounted therein, in accordance with the present invention. The conformal placement element 30 includes a first surface 32 (not shown) and a second surface 34 opposite the first surface 32. The conformal placement element 30 has a compliant structure 40 that conforms to a patient's body upon placement of the first surface 32 thereon. The compliant structure 40 can be configured to conform to a skin surface on a patient's body. In accordance with an example embodiment, the compliant structure 40 conforms to a part of patient's body selected from the group consisting of a deltoid, an upper arm, a calf, a thigh, a forearm, an upper back, and a lower back.

In accordance with an example embodiment, the compliant structure 40 is formed from a material selected from the group consisting of open celled foam, closed cell foam, natural rubber, synthetic rubber, and thermoplastic elastomer. In accordance with an example embodiment, the compliant structure 40 is formed from a polyurethane foam. In accordance with an example embodiment, the compliant structure 40 is formed from a black polyurethane foam. In accordance with an example embodiment, the compliant structure 40 is formed from a die-cut polyurethane foam (e.g., commercially available Sekisui 6EO 0.031 BLK polyurethane foam).

Figure 2A:
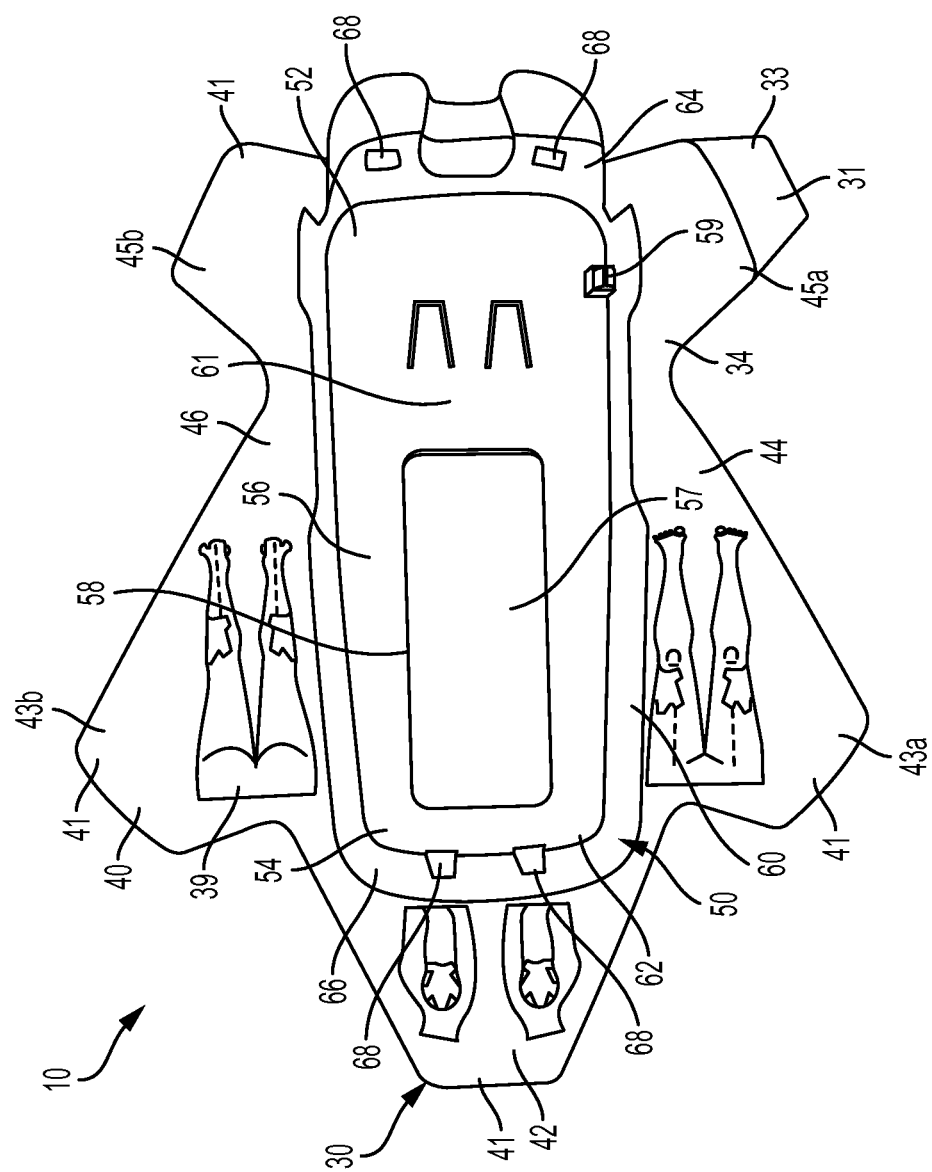
FIG. 2A is the top view of the patient interface of FIG. 1, showing the shoe when the reusable optical sensor is not removably mounted in the shoe.
Figure 2B:
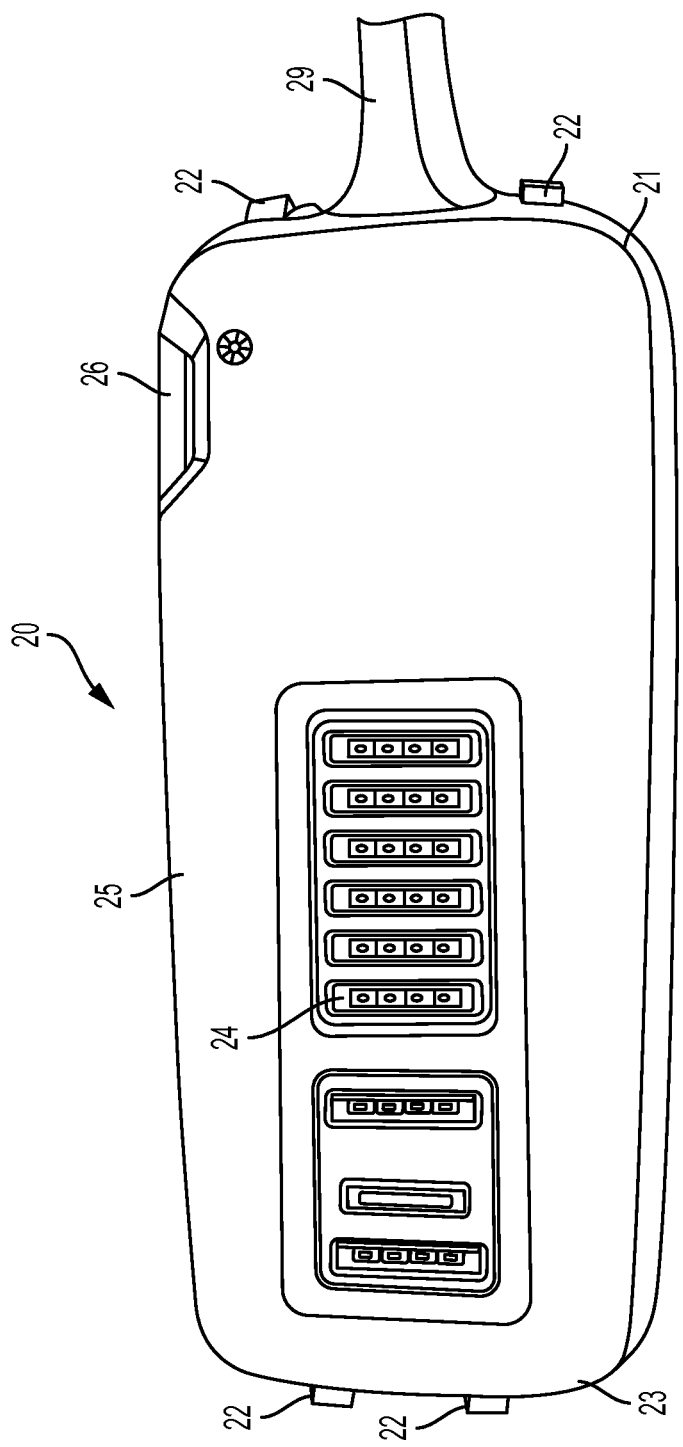
FIG. 2B is a top view of the reusable sensor of FIG. 1.

Turning now to FIGS. 2A and 2B, there are depictions of an example embodiment of the patient interface 10 without the reusable optical sensor 20 removably mounted in the shoe 50 (FIG. 2A) and an example embodiment of a reusable optical sensor 20 (FIG. 2B). As shown in FIG. 2A, an example embodiment of the patient interface 10 includes a shoe 50 fixed with the second surface 34 of the conformal placement element 30. The shoe 50 is configured to removably receive the reusable optical sensor 20. The shoe 50 includes a heel portion 52, a toe portion 54, a medial portion 56 therebetween, a base 61 positioned against the second surface 34 of the conformal placement element 30 from the heel portion 52 to the toe portion 54, and a barrier 60 extending around a perimeter 62 of the base 61. The barrier 60 includes a first wall portion 64 and a second wall portion 66 opposite to the first wall portion 64. The first wall portion 64 and the second wall portion 66 each include at least one aperture 68 which removably locks with at least one protrusion 22 (see FIG. 2B) on the reusable optical sensor 20. Referring briefly to FIG. 1, the barrier 60 frames the reusable optical sensor 20 when the reusable optical sensor 20 is removably mounted in the shoe 50 when the at least one aperture 68 is removably locked with the at least one protrusion 22. The shoe 50 can be constructed from using a variety of materials, such as a thermoplastic alloy, for example, containing polycarbonate, polyethylene terephthalate, high density polyethylene, polyvinyl chloride or polypropylene. In accordance with an example embodiment, the shoe 50 is constructed from a thermoplastic alloy that includes a blend of polycarbonate and acrylonitrile-butadiene-styrene (e.g., commercially available from Polymer Resources of Farmington, Conn.). In accordance with an example embodiment, the barrier 60 is opaque, for example, to prevent ambient light from passing through the barrier 60 and interfering with the sensor optics.

Looking back again at FIGS. 2A and 2B, although there is shown the first wall portion 64 and the second wall portion 66 proximal the heel portion 52 and the toe portion 54, respectfully, it should be appreciated that the first wall portion 64 and the second wall portion 66 can be positioned proximal the first side 44 of the shoe 50 and the second side 46 of the shoe 50, respectively. In accordance with an example embodiment, the barrier 60 can include at least one aperture 68 proximal the first side 44 of the shoe 50 and at least one aperture 68 proximal the second side 46 of the shoe 50. It should be appreciated that the location of the at least one aperture 68 and the at least one protrusion 22 can vary depending on the application, as long as they are positioned in a way that permits the at least one aperture 68 to removably lock with the at least one protrusion 22. It should also be appreciated that the number of the at least one aperture 68 and the at least one protrusion 22 included in the shoe 50 and the reusable optical sensor 20, respectively, can vary, depending on the application, as will be appreciated by the skilled artisan. Although the example embodiment depicted in FIGS. 2A and 2B shows two of the at least one aperture 68 and two of the at least one protrusion 22 proximal the heel portion 52 and the toe portion 54, the patient interface 10 can be configured with greater or fewer of the at least one aperture 68 and the at least one protrusion 22, as will be appreciated by the skilled artisan. In accordance with an example embodiment, the first wall portion 64 and the second wall portion 66 each include one of the at least one aperture 68 and one of the at least one protrusion 22. In accordance with an example embodiment, the first wall portion 64 and the second wall portion 66 each include three of the at least one aperture 68 and three of the at least one protrusion 22.

The shoe 50 includes an opening 57 passing completely through the base 61 proximal the medial portion 56 of the shoe 50. The opening 57 is provided with a perimeter 58 that frames the optical elements 24 proud from the reusable optical sensor 20, as is discussed in further detail in connection with FIG. 2B below.

Still looking at FIG. 2A, it can be seen that the compliant structure 40 includes a plurality of wings 41. Although the compliant structure 40 shown in the example embodiment in FIG. 2A has five wings, the skilled artisan will appreciate that the number and size of the plurality of wings 41 can vary, depending on the application. Generally, the plurality of wings 41 collectively cause optical elements of the sensor to rest flush against the patient's body when the compliant structure 40 conforms to the patient's body without permitting ambient air or light to pass between the optical elements and the patient's body. In addition, the plurality of wings 41 are collectively configured to adhere to skin on the patient's body without causing wrinkles to form in the plurality of wings 41. The compliant structure 40, including the plurality of wings 41, can define a curved shape, and sized and configured to conform to a part of the patient's body, as noted above. Specifically, the shape of the curved perimeter can be configured to generally follow and accommodate curved anatomical surfaces of a patient in such a way as to prevent the compliant structure 40 from forming wrinkles when applied against the curved anatomical surfaces of the patient, as would be appreciated by those of skill in the art.

In accordance with the example embodiment shown in FIG. 2A, at least one of the plurality of wings 41 includes an instructional diagram 39 illustrating proper placement and location of the patient interface 10 against the patient's body. Typically, the instructional diagram 39 is disposed within the field of view of a user as they place the patient interface 10 against the patient's body, enabling a user to properly place the patient interface 10 against the patient's body while simultaneously looking at the patient's body until the patient interface 10 is properly placed. In this way, the instructional diagram 39 facilitates rapid placement of the sensor, for example, in emergency situations, and also enables even less skilled user's to properly and rapidly place the sensor without taking their eyes off of the patient. Generally, the plurality of wings 41 includes an instructional diagram 39 illustrating proper placement on the location of the patient's body for which the compliant structure 40 was configured to conform. By way of example, the compliant structure 40 shown in the example embodiment depicted in FIG. 2A is configured to conform to rounded muscles such as the deltoid, thigh, and calf and therefore includes an instructional diagram 39 for each of those locations on the patient's body. As shown in FIG. 2A, the instructional diagram 39 can illustrate proper placement on both left and right sides of a patient's body, including dotted or dashed lines to indicate the midpoint of certain body locations, such as the thigh and calf. The instructional diagram 39 can show both left and right views in a single diagram depicting a patient's body (e.g., thigh or calf), or in multiple diagrams (e.g., deltoid). Although FIG. 2A shows an instructional diagram 39 disposed on three of the plurality of wings 41, it should be appreciated that one or more instructional diagrams 39 can be placed on any of the wings, as desired. For example, each of the plurality of wings 41 can include one instructional diagram 39. As another example, one of the plurality of wings 41 can include two or more instructional diagrams 39. The skilled person can readily envision the various permutations of placement of instructional diagrams 39 on the plurality of wings 41.

In accordance with the example embodiment shown in FIG. 2A, the plurality of wings 41 includes a first wing 42 proximal the toe portion 54, a second wing 43a positioned proximal the medial portion 56 on a first side 44 of the shoe 50, a third wing 43b positioned proximal the medial portion 56 on a second side 46 of the shoe 50 opposite the second wing 43a, a fourth wing 45a positioned proximal the heel portion 52 on the first side 44 of the shoe 50, and a fifth wing 45b positioned proximal the heel portion 52 on the second side 46 of the shoe 50 opposite the fourth wing 45a. In accordance with an example embodiment, the first wing 42 has a nominal dimension of 52 mm±10 mm extending from the top edge of the opening 58. The first wing 42 secures the toe portion 54 of the shoe 50 in place when the first wing 42 conforms to muscle underlying skin on the patient's body. In accordance with an example embodiment, the first wing 42 adheres to skin on the patient's body without causing wrinkles to form in the plurality of wings 41. The second wing 43a and the third wing 43b form a first pair of wings 43a, 43b which are sized and dimensioned to conform to muscle underlying skin on the patient's body. In accordance with an example embodiment, the first pair of wings 43a, 43b are sized and dimensioned to conform to muscle underlying skin on the patient's body without substantially diminishing adhesion between the first pair of wings 43a, 43b and the skin on the patient's body. In accordance with an example embodiment, the span of the second wing 43a to the third wing 43b has a nominal dimension of 144 mm±20 mm extending from wing tip to wing tip. In accordance with an example embodiment, the first pair of wings 43a, 43b are symmetrical. The fourth wing 45a and the fifth wing 45b form a second pair of wings 45a, 45b which are sized and dimensioned to secure the heel portion 52 of the shoe 50 in place when the second pair of wings 45a, 45b conform to muscle underlying skin on the patient's body. In accordance with an example embodiment, the span of the fourth wing 45a to the fifth wing 45b has a nominal dimension of 105 mm±20 mm extending from wing tip to wing tip. The second pair of wings 45a, 45b adhere to skin on the patient's body without causing wrinkles to form in the plurality of wings 41. In accordance with an example embodiment, the second pair of wings 45a, 45b are symmetrical. In accordance with an example embodiment, the nominal angles between the first wing 42 and the second wing 43a and between the first wing 42 and the third wing 43b are 92°±10°. In accordance with an example embodiment, the nominal angles between the second wing 43a and the fourth wing 45a and between the third wing 43b and the fifth wing 45b are 95°±10°.

In accordance with an example embodiment, at least one of the plurality of wings 41 comprises a tab 31, which is a continuation of a removable liner 33 and extends beyond a perimeter edge of the compliant structure 40, enabling removal of the removable liner 33 from the compliant structure 40. Although FIG. 2A shows the tab 31 extending beyond a perimeter edge of the compliant structure 40 proximal the fourth wing 45a, it should be appreciated that the tab 31 can extend beyond the perimeter edge of the compliant structure 40 proximal any of the plurality of wings 41, as the invention is not intended to be limited by the location of the tab 31.

Turning now to FIG. 2B, there is depicted a patient facing side of an example embodiment of a reusable optical sensor 20 for use with patient interface 10 (not shown). The present invention contemplates using any reusable optical sensor 20 for which a disposable patient interface 10 is desirable. In accordance with an example embodiment, the reusable optical sensor 20 comprises a spectroscopic-based reusable optical sensor 20 that measures multiple parameters (such as, for example SmO2, pH and/or Hct) that are valuable in the care of trauma and other critically ill patients. See, the type disclosed in U.S. Publication No. 2011/0205535, the disclosure of which is incorporated herein in its entirety. In accordance with an example embodiment, the reusable optical sensor 20 can be applied on the battlefield, at the scene of an accident, in an emergency transport vehicle or in the operating room, the ICU, emergency room or other parts of a hospital. In some instances, the reusable optical sensor 20 can be attached to a patient's body for many days. In accordance with an example embodiment, the reusable optical sensor 20 can be used during sports and exercise. See, U.S. Publication No. 2009/0024013, the disclosure of which is incorporated herein in its entirety, or at home for monitoring patients with chronic diseases.

The patient interface 10 is a disposable patient interface 10 intended for use with a reusable optical sensor 20. The patient interface 10 possesses a security mechanism that prevents the reusable optical sensor 20 from operating when the reusable optical sensor 20 is not removably mounted in the shoe 50. In this way, the patient interface 10 assures that a user does not use the reusable optical sensor 20 without a disposable patient interface 10. In accordance with an example embodiment, the reusable optical sensor 20 comprises a security sensor which prevents the reusable optical sensor 20 from operating when the reusable optical sensor 20 is not removably mounted in the shoe 50. In accordance with an example embodiment, the security sensor comprises a hall sensor including the security sensor and a magnet 59 coupled to the base 61, as depicted in FIGS. 2A and 4, wherein the magnet 59 generates a magnetic field that can only be detected by the reusable optical sensor 20 when the reusable optical sensor 20 is removably mounted in the shoe 50. It is contemplated that any suitable method can be used to couple the magnet 59 to the base 61, for example, by fastening (e.g., gluing) the magnet 59 to the base 61. Other security measures can also be used such as an RFID or other electronic chip disposed on the patient interface 10 that can be detected by a receiver on the reusable optical sensor 20.

As shown in the example embodiment in FIG. 2B, the reusable optical sensor 20 includes a first end 21 proximal a cable 29 and a second end 23 opposite the first end 21, and optical elements 24 disposed between the first end 21 and the second end 23. Although the example embodiment shown in FIG. 2B depicts the cable 29 proximal the first end 21, it should be appreciated that the reusable optical sensor 20 can be wireless. For example, instead of a cable 29, the reusable optical sensor 20 can include a case extension e.g., tail (not shown) that facilitates rapid removal of the reusable optical sensor 20, as described further below. In some implementations, the case extension includes an antenna for wireless communication. The optical elements 24 are proud from a surface of sensor case 25 so that when the reusable optical sensor 20 is removably mounted in the shoe 50 as shown in FIG. 1, the optical elements 24 contact the base 61 of the shoe 50 as they extend through the opening 57 into contact with the optical film shown in FIG. 5A covering the opening 57. The reusable optical sensor 20 can also include at least a portion that is indented 26 for receiving a magnet 59 (shown in FIG. 2A) coupled to the base 61. As noted above, at least one protrusion 22 is disposed proximal the first end 21 and the second end 23 for removably locking with the at least one aperture 68 of the shoe 50. In accordance with the example embodiment shown in FIG. 2B, the at least one protrusion 22 includes two protrusions. The at least one protrusion 22 is sized and dimensioned with the same shape but smaller size as the at least one aperture 68, for example, to permit the at least one protrusion 22 to removably lock with the at least one aperture 68. It should be appreciated that the at least one protrusion 22 can have any three dimensional shape as long as it is capable of locking with the corresponding at least one aperture 68 of the shoe 50, as will be appreciated by the skilled artisan. In the example embodiment shown in FIG. 2B, the shape of the at least one protrusion 22 is quadrilateral, however, other shapes are contemplated (e.g., square, rectangular, triangular, spherical, etc.). In accordance with an example embodiment, the at least one protrusion 22 includes a rounded edge (not shown), for example, to permit rapid locking and unlocking with the at least one aperture 68. That way, the reusable optical sensor 20 can be rapidly inserted from the patient interface 10, as shown in FIGS. 3A and 3B, as well as rapidly removed using the features shown in FIG. 4.

Figure 3A:
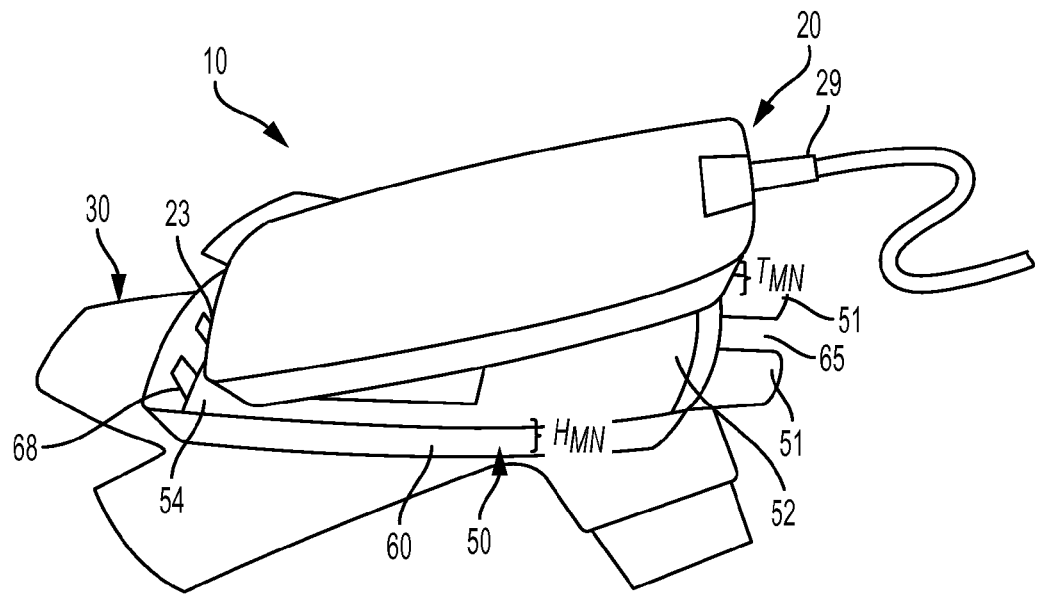
FIG. 3A is a diagrammatic illustration depicting a perspective view of the patient interface of FIG. 1, showing the reusable optical sensor being removably mounted in the shoe, in accordance with an example embodiment of the present invention.
Figure 3B:
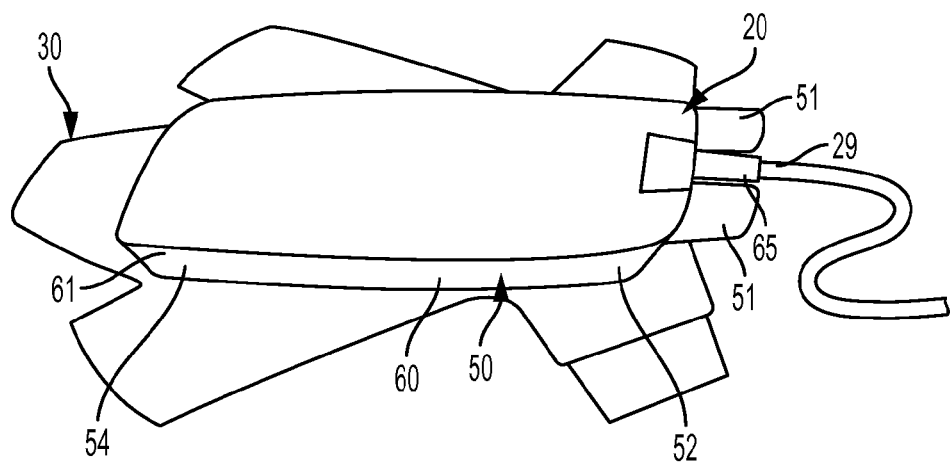
FIG. 3B is a diagram depicting a perspective view of the patient interface of FIG. 3B, showing the reusable optical sensor removably mounted in the shoe with a barrier of the shoe framing the reusable optical sensor.

Referring first to FIGS. 3A and 3B, there are shown diagrams depicting perspective views of the patient interface 10 illustrating the reusable optical sensor 20 being removably mounted in the shoe 50 (FIG. 3A) and the reusable optical sensor 20 in a final removably mounted configuration in the shoe 50 (FIG. 3B) with the at least one aperture 68 being removably locked with the at least one protrusion 22. As shown in FIG. 3A, the reusable optical sensor 20 can be removably mounted in the shoe 50 by sliding the second end 23 of the reusable optical sensor 20 toward the barrier 60 proximal the toe portion 54 of the shoe 50 so that the at least one protrusion 22 proximal the second end 23 of the reusable optical sensor 20 removably locks with the at least one aperture 68 proximal the toe portion 54 of the shoe 50. Once removably locked, the first end 21 of the reusable optical sensor 20 can be pushed toward the base 61 proximal the heel portion 52 of the shoe 50 so that the at least one protrusion 22, as depicted in FIG. 2B, proximal the first end 21 of the reusable optical sensor 20 removably locks with the at least one aperture 68, as depicted in FIG. 2A, proximal the heel portion 52 of the shoe 50, thereby removably mounting the reusable optical sensor 20 in the shoe 50 as is shown in FIG. 3B.

FIG. 3B shows the barrier 60 framing the reusable optical sensor 20 when the reusable optical sensor 20 is removably mounted in the shoe 50, and when the at least one aperture 68 is removably locked with the at least one protrusion 22. In other words, the size and dimension of the shoe 50 are slightly larger than the size and dimension of the reusable optical sensor 20, for example, to ensure that the reusable optical sensor 20 remains secure when removably mounted in the shoe 50. This configuration of the shoe 50 permits rapid insertion and removal of the reusable optical sensor 20 by permitting the reusable optical sensor 20 to be removably mounted in the shoe 50 in such a way that the barrier 60 framing the reusable optical sensor 20 does not impede sensor insertion or sensor removal. This is achieved, in part, by providing the barrier 60 with a minimal height dimension ($H_{min}$) that is equal to or greater than a minimum thickness dimension ($T_{min}$) of the reusable optical sensor 20. That way, the barrier 60 is high enough to prevent ambient light from passing between the sensor and the shoe 50.

Turning now to FIG. 4, there is shown another view of the patient interface 10, highlighting features of the patient interface 10 which permit rapid removal of the reusable optical sensor 20 when the reusable optical sensor 20 is removably mounted in the shoe 50. For example, the shoe 50 can include at least one tab or actuator 51 projecting from the barrier 60 proximal the heel portion 52, for example, to unlock the at least one protrusion 22 from the at least one aperture 68 to dismount the sensor from the shoe 50. When pressed, the at least one actuator 51 causes a flexing motion of the shoe 50, which in turn causes the at least one protrusion 22 proximal either the first wall portion 64 or the second wall portion 66 to unlock from the at least one aperture 68 removably locked with the at least one protrusion 22 proximal either the first wall portion 64 or the second wall portion 66, which in turn causes at least a portion of the reusable optical sensor 20 proximal the heel portion 52 to dismount from the shoe 50. In accordance with an example embodiment, the at least one actuator 51 comprises a depression 53 which provides a visual cue for a user to press the at least one actuator 51 when the user wishes to dismount the reusable optical sensor 20 from the shoe 50, for example, to sterilize or clean and reuse the optical sensor 20. The configuration of the at least one actuator 51 allows a user to rapidly dismount the optical sensor 20 using a single hand when the sensor is removably mounted in the shoe 50, for example, by depressing the depression 53 on the at least one actuator 51 with a thumb while grasping the sensor cable 29 or other extension of the sensor case 25 (e.g., tail) with the fingers of the same hand. Of course, a user can rapidly remove the sensor using both hands by depressing both at least one actuator 51, for example, using thumbs while wrapping their fingers from at least one hand around the sensor cable 29 or the end of the sensor case 25 extension (e.g., tail, e.g., of a wireless sensor) and pulling or lifting the sensor cable 29 away from the patient interface 10. Although the example embodiment shown in FIG. 4 depicts two of the at least one actuator 51 projecting from the barrier 60 proximal the heel portion 52, it should be appreciated that the at least one actuator 51 can be configured as a single actuator. As shown in FIG. 4, the two at least one actuators 51 projecting from the barrier 60 proximal the heel portion 52 can be coupled to each other via an inverted bridge 63 that provides a gap 65 through which a sensor cable 29 (if present) or case extension can pass without interfering with insertion or removal of the sensor, as is illustrated in FIG. 3B. In accordance with an example embodiment, depression 53 of at least one of the two actuators while simultaneously pulling or lifting the cable 29 case extension enables a user to rapidly dismount the reusable optical sensor 20 from the disposable patient interface 10 using a single hand.

Still looking at FIG. 4, the shoe 50 can optionally include at least one elastic spring energy storage element 55 disposed on the base 61 proximal the heel portion 52 to assist with rapid removal of the sensor. The at least one elastic spring energy storing element stores elastic spring energy when elastically deformed into a first position, substantially co-planar with the base 61 when the reusable optical sensor 20 is removably mounted in the shoe 50. The at least one elastic spring energy storage element 55 transfers elastic energy stored therein to the reusable optical sensor 20 when the at least one elastic energy storage element springs to a second position angled away from the plane of the base 61 and toward the reusable optical sensor 20, pushing the reusable optical sensor 20 to be dismounted from the shoe 50.

Figure 5A:
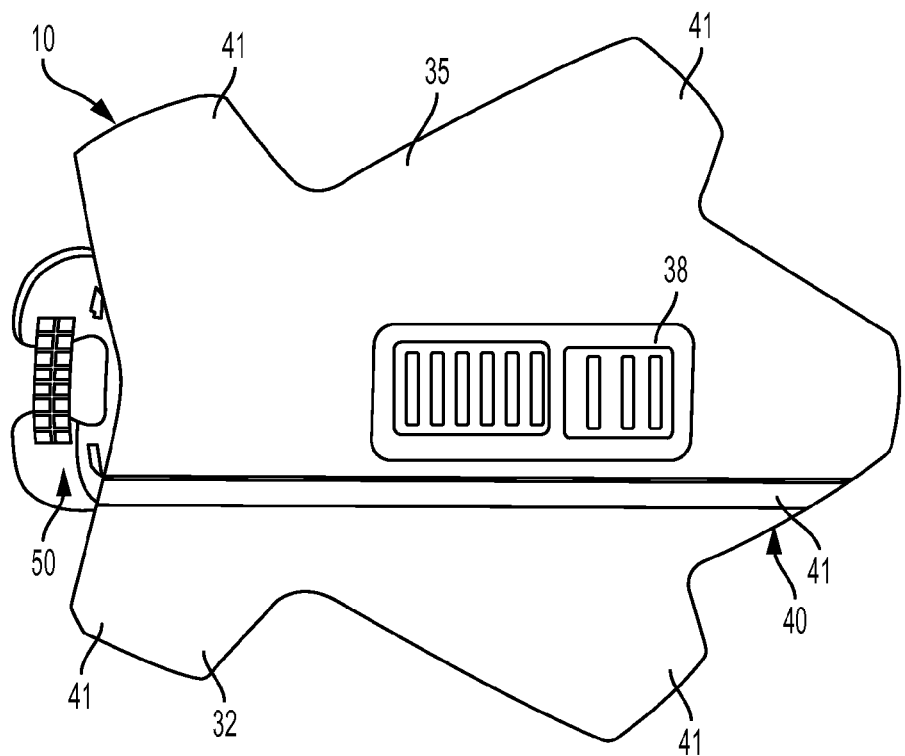
FIG. 5A is a bottom view of the patient interface of FIG. 1, illustrating the conformal placement element after the removable liner has been removed.
Figure 5B:
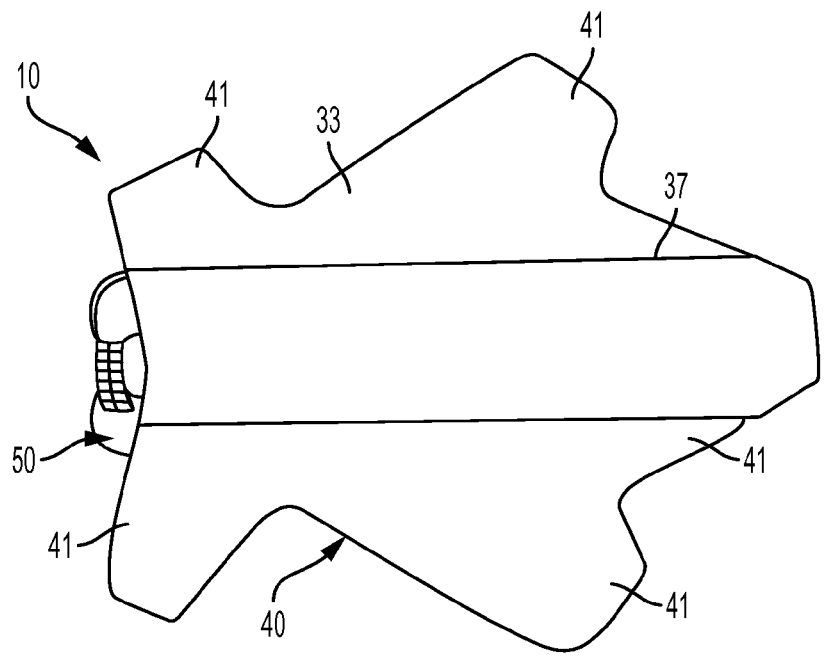
FIG. 5B is a photograph depicting a bottom view of the patient interface of FIG. 1, showing a removable liner adhered to a conformal placement element.

Referring now to FIGS. 5A and 5B, there are shown representations of the present invention depicting the patient facing side of the patient interface 10 before removal of a removable liner 33 (see FIG. 5B) and after removal of the removable liner 33 (see FIG. 5A). Looking first at FIG. 5A, an adhesive layer 35 with biocompatible components can be disposed on at least a portion of the first surface 32 of the conformal placement element 30. The adhesive layer 35 can include a transfer adhesive, such as the 2120U or RX1311U transfer adhesive commercially available from Avery Dennison and Scapa respectively. The transfer adhesive is preferably sufficiently strong to keep the patient interface 10 securely in place during sensor measurements, while also allowing removal from the patient's body without damaging the skin. The transfer adhesive is preferably very thin, and may be used to maintain the flexibility of the plurality of wings 41, such that the compliant structure 40 may be conformed to rounded muscles of varying size, shape, and contour. An optically clear window 38 may be aligned with the opening 57 in the base 61 of the shoe 50. The optically clear window 38 may include an adhesive surface along at least a portion thereof. The optically clear window 38 may include, for example, an optical tape such as 9793R polyolefin diagnostic tape available from 3M. The optical tape preferably transmits light through a thickness of the tape, but does not transmit light longitudinally along a length of the tape. Longitudinal light transmission may interfere with sensor measurements, e.g., light from the sensor LEDs may be transmitted directly to the detector. The inside surface of the optically clear window 38 may be free of adhesive. In use, the optical sensor 20 is held directly against optical tape, such that there is substantially no air gap between the optical sensor 20 and the optically clear window 38. Preferably, the combined thickness of the shoe 50, compliant structure 40 and adhesive layer 35 cause a protrusion of the sensor optical elements 24 into the optically clear window 38. In accordance with an example embodiment, the sum of thickness of the shoe 50, compliant structure 40 and adhesive layer 35 is nominally 1.967 mm±0.27 mm.

Turning now to FIG. 5B, the adhesive element may include a removable liner 33 proximate the adhesive layer 35. In some embodiments, the removable liner 33 is optically transparent in the near infrared region. A suitable optically clear liner is a 2 mil PET CIS Coating F-36 available from MP1. Having an optically transparent removable liner 33 may provide the benefit of enabling measurements, calibrations, sensor checking, and other steps to be carried out prior to removing the liner and adhering the patient interface 10 to the patient. In accordance with an example embodiment, at least a portion 37 of the removable liner 33 is sufficiently opaque to prevent a user from using the reusable optical sensor 20 without first removing the liner.

Figure 6:
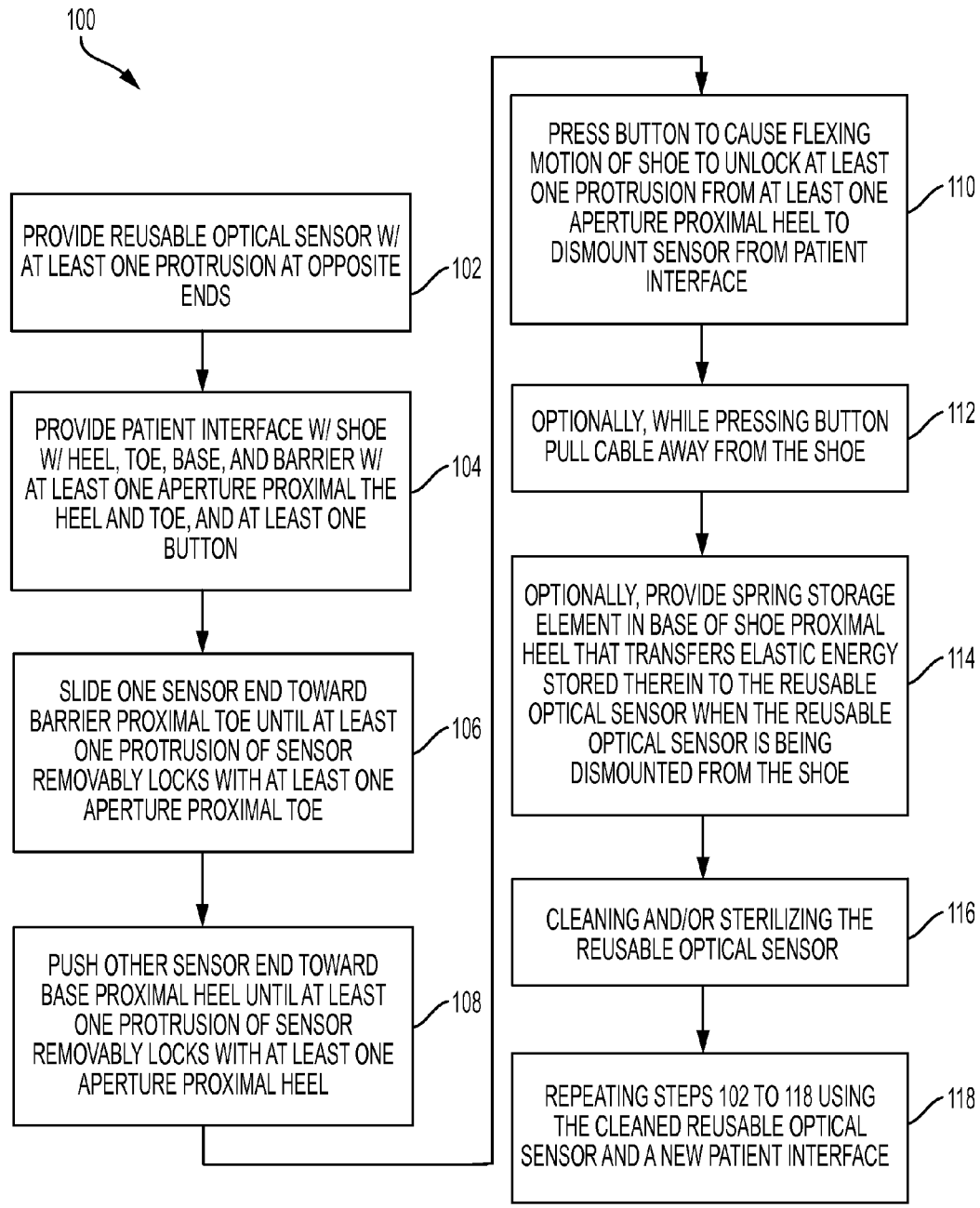
FIG. 6 is a flowchart depicting a method of mounting and dismounting a reusable optical sensor in a disposable patient interface, in accordance with aspects of the present invention.

Turning now to FIGS. 6 and 7, there is shown operation of the patient interface 10. In operation, a reusable optical sensor 20 can be removably mounted in the patient interface 10 by performing steps 102 through 108 of method 100. When the sensor is removably mounted in the patient interface 10, the patient interface 10 can be placed against a patient's body by performing steps 202 and 204 of method 200. Measurements can be obtained using the sensor when properly placed against the patient's body. When the measurements are obtained, the reusable optical sensor 20 can be optionally dismounted by performing steps 110 through 114 of method 100, and the patient interface 10 can be removed from the patient's skin and discarded. If desired, the reusable optical sensor 20 can be sterilized and/or cleaned in step 116 of method 100. If desired, each of the above steps can be repeated (step 118).

With particular reference now to FIG. 6, there is shown a flowchart illustrating an example embodiment of a method 100 for removably mounting a reusable optical sensor 20 in a disposable patient interface 10. Method 100 begins with a step 102 of providing a reusable optical sensor 20 as described herein. In accordance with an example embodiment, the reusable optical sensor 20 includes a first end 21 proximal a cable 29 or case extension of the sensor and a second end 23 opposite the first end 21, as is illustrated in FIG. 2B. Next, method 100 proceeds with a step 104 of providing a disposable patient interface 10 as described herein. In accordance with an example embodiment, the disposable patient interface 10 includes a conformal placement element 30, a shoe 50, and at least one actuator 51. The conformal placement element 30 has a compliant structure 40 that conforms to a patient's body upon placement thereon. The shoe 50 is fixed with the conformal placement element 30, removably receives a reusable optical sensor 20. The shoe 50 includes a heel portion 52, a toe portion 54, a medial portion 56 therebetween, a base 61 positioned against the second surface 34 of the conformal placement element 30 from the heel portion 52 to the toe portion 54, and a barrier 60 extending around a perimeter 62 of the base 61. The barrier 60 includes a first wall portion 64 and a second wall portion 66 opposite to the first wall portion 64. The first wall portion 64 and the second wall portion 66 each include at least one aperture 68 which removably locks with at least one protrusion 22 on the reusable optical sensor 20, and at least one actuator 51 projecting from the barrier 60 proximal the heel portion 52. Method 100 then proceeds with a step 106 of sliding the second end 23 of the sensor toward the barrier 60 proximal the toe portion 54 of the shoe 50 so that the at least one protrusion 22 proximal the second end 23 of the reusable optical sensor 20 removably locks with the at least one aperture 68 proximal the toe portion 54 of the shoe 50. Method 100 then proceeds with a step 108 of pushing the first end 21 of the reusable optical sensor 20 toward the base 61 proximal the heel portion 52 of the shoe 50 so that the at least one protrusion 22 proximal the first end 21 of the reusable optical sensor 20 removably locks with the at least one aperture 68 proximal the heel portion 52 of the shoe 50, thereby removably mounting the reusable optical sensor 20 in the disposable patient interface 10. As noted above, the disposable patient interface 10 with the reusable optical sensor 20 removably mounted in the shoe 50 is ready for use by placing the patient interface 10 against a patient's body, for example, using method 200.

When the measurements are obtained using the patient interface 10, method 100 can proceed to steps 110-114 for dismounting the reusable optical sensor 20. In accordance with an example embodiment, dismounting the reusable optical sensor 20 includes a step 110 of pressing the at least one actuator 51 to cause a flexing motion of the shoe 50, which in turn causes the at least one protrusion 22 proximal either the first wall portion 64 or the second wall portion 66 to unlock from the at least one aperture 68 removably locked with the at least one protrusion 22 proximal either the first wall portion 64 or the second wall portion 66, which in turn causes at least a portion of the reusable optical sensor 20 proximal the heel portion 52 to dismount from the shoe 50. Optionally, method 100 includes a step 112 of pulling or lifting a cable 29 or the end of the sensor case extension disposed proximal the first end 21 of the sensor away from the shoe 50, wherein the pressing and pulling or lifting are optionally performed using a same hand of the user, thereby dismounting the sensor from the patient interface 10. Optionally, method 100 includes a step 114 of providing a spring storage element 55 disposed in base 61 of shoe 50 proximal the heel that transfers elastic energy stored therein to the reusable optical sensor 20 when the at least one elastic energy storage element springs 55 to a position angled away from the plane of the base 61 and toward the reusable optical sensor 20, pushing the reusable optical sensor 20 to be dismounted from the shoe 50. The disposable patient interface 10 can be discarded by the user, followed by a step 116 of cleaning and/or sterilizing the reusable optical sensor 20. Any suitable technique available to the skilled artisan can be used to clean and/or sterilize the sensor for reuse.

Turning now to FIG. 7, there is shown a flowchart illustrating an example embodiment of a method 200 for placing a disposable patient interface 10 on a patient's body. Method 200 begins with a step 202 of providing a patient interface 10 as described herein. In accordance with an example embodiment, the patient interface 10 includes a conformal placement element 30 that has a compliant structure 40 that conforms to a patient's body upon placement thereon, wherein the compliant structure 40 comprises a plurality of wings 41, at least one of which comprises an instructional diagram 39 disposed within the field of view of a user illustrating proper placement and location of the patient interface 10 against the patient's body, a shoe 50 fixed with the conformal placement element 30, and a reusable optical sensor 20 removably mounted in the shoe 50. Method 200 then proceeds with a step 204 of placing the patient interface 10 against the patient's body while simultaneously looking at the patient interface 10 and the patient's body until the patient interface 10 is properly placed.

The patient interface 10 of the present invention permits rapid mounting of a reusable optical sensor 20 in a disposable patient interface 10 before use. The patient interface 10 enables a user to properly place the patient interface 10 against the patient's body while simultaneously looking at the patient's body until the patient interface 10 is properly placed. The patient interface 10 ensures that optical elements 24 of a reusable optical sensor 20 rest flush against the patient's body while the patient interface 10 conforms to the patient's body without permitting ambient air or light to pass between the optical elements 24 and the patient's body. The patient interface 10 includes a compliant structure 40 that is sized and dimensioned to conform to the patient's body without causing wrinkles to form in the compliant structure 40, for example, to maximize adhesion between the patient interface 10 and the patient's skin during operation of the sensor. The patient interface 10 of the present invention enables a user to rapidly dismount or dislodge a reusable optical sensor 20 from a disposable patient interface 10 using a single hand. The patient interface 10 of the present invention prevents operation of the sensor when the sensor is not removably mounted in the patient interface 10. The patient interface 10 of the present invention ensures that the patient interface 10 is properly placed against a patient's skin during operation of the sensor.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A patient interface for a reusable optical sensor, the patient interface comprising:
   a conformal placement element comprising a first surface and a second surface opposite the first surface, wherein the conformal placement element has a compliant structure which conforms to a patient's body upon placement of the first surface thereon; and
   a shoe fixed with the second surface of the conformal placement element and which is adapted to removably receive a reusable optical sensor, the shoe comprising a heel portion, a toe portion, a medial portion therebetween, a base positioned against the second surface of the conformal placement element from the heel portion to the toe portion, and a barrier extending around a perimeter of the base, the barrier comprising a first wall portion and a second wall portion opposite to the first wall portion, the first wall portion and the second wall portion each comprising at least one aperture which is adapted to removably lock with at least one protrusion on the reusable optical sensor,
   wherein the barrier frames the reusable optical sensor when the reusable optical sensor is removably mounted in the shoe when the at least one aperture is removably locked with the at least one protrusion;
   wherein the compliant structure comprises a plurality of wings which collectively cause optical elements of the sensor to rest flush against the patient's body when the compliant structure conforms to the patient's body without permitting ambient air or light to pass between the optical elements and the patient's body; and
   wherein the plurality of wings comprises:
      a first wing proximal the toe portion,
      a second wing positioned proximal the medial portion on a first side of the shoe,
      a third wing positioned proximal the medial portion on a second side of the shoe opposite the second wing,
      a fourth wing positioned proximal the heel portion on the first side of the shoe, and
      a fifth wing positioned proximal the heel portion on the second side of the shoe opposite the fourth wing.

2. The interface of claim 1, wherein the compliant structure comprises a material selected from the group consisting of open celled foam, closed cell foam, natural rubber, synthetic rubber, black polyurethane foam, and thermoplastic elastomer.

3. The interface of claim 1, wherein the compliant structure conforms to a part of patient's body selected from the group consisting of a deltoid, an upper arm, a calf, a thigh, a forearm, an upper back, and a lower back.

4. The interface of claim 1, wherein at least one of the plurality of wings comprises an instructional diagram illustrating proper placement and location of the patient interface against the patient's body.

5. The interface of claim 4, wherein the instructional diagram is disposed within a field of view of a user as the user places the patient interface against the patient's body, enabling the user to properly place the patient interface against the patient's body while simultaneously looking at the patient's body until the patient interface is properly placed.

6. The interface of claim 1, wherein the first wing secures the toe portion of the shoe in place when the first wing conforms to muscle underlying skin on the patient's body and adheres to skin on the patient's body without causing wrinkles to form in the plurality of wings.

7. The interface of claim 1, wherein the second wing and the third wing comprise a first pair of wings which are sized and dimensioned to conform to muscle underlying skin on the patient's body and adhere to skin on the patient's body without causing wrinkles to form in the plurality of wings.

8. The interface of claim 1, wherein the fourth wing and the fifth wing comprise a second pair of wings which are sized and dimensioned to secure the heel portion of the shoe in place when the second pair of wings conform to muscle underlying skin on the patient's body and adhere to skin on the patient's body without causing wrinkles to form in the plurality of wings.

9. The interface of claim 1, wherein the shoe further comprises an opening passing completely through the base proximal the medial portion of the shoe, wherein the opening comprises a perimeter that is adapted to frame optical elements proud from the reusable optical sensor.

10. The interface of claim 9, further comprising an optically clear window aligned with the opening.

11. The interface of claim 1, further comprising a removable liner, wherein at least a portion of the removable liner is sufficiently opaque to prevent a user from using the reusable optical sensor without first removing the removable liner.

12. The interface of claim 1, wherein the reusable optical sensor comprises a security sensor which prevents the reusable optical sensor from operating when the reusable optical sensor is not removably mounted in the shoe.

13. The interface of claim 12, wherein the security sensor comprises a hall sensor and the shoe comprises a magnet coupled to the base, wherein the magnet generates a magnetic field that can only be detected by the hall sensor of the reusable optical sensor when the reusable optical sensor is removably mounted in the shoe.

14. The interface of claim 1, wherein the barrier is opaque.

15. The interface of claim 1, wherein the barrier has a minimal height dimension that is equal to or greater than a minimum thickness dimension of the reusable optical sensor.

16. The interface of claim 1, wherein the reusable optical sensor comprises at least a portion that receives a magnet coupled to the base.

17. A patient interface for a reusable optical sensor, the patient interface comprising:
a conformal placement element comprising a first surface and a second surface opposite the first surface, wherein the conformal placement element has a compliant structure which conforms to a patient's body upon placement of the first surface thereon; and
a shoe fixed with the second surface of the conformal placement element and which is adapted to removably receive a reusable optical sensor, the shoe comprising a heel portion, a toe portion, a medial portion therebetween, a base positioned against the second surface of the conformal placement element from the heel portion to the toe portion, and a barrier extending around a perimeter of the base, the barrier comprising a first wall portion and a second wall portion opposite to the first wall portion, the first wall portion and the second wall portion each comprising at least one aperture which is adapted to removably lock with at least one protrusion on the reusable optical sensor,
wherein the barrier frames the reusable optical sensor when the reusable optical sensor is removably mounted in the shoe when the at least one aperture is removably locked with the at least one protrusion,
wherein the shoe further comprises at least one actuator projecting from the barrier proximal the heel portion, wherein when pressed the at least one actuator causes a flexing motion of the shoe, which in turn causes the at least one protrusion proximal either the first wall portion or the second wall portion to unlock from the at least one aperture removably locked with the at least one protrusion proximal either the first wall portion or the second wall portion, which in turn causes at least a portion of the reusable optical sensor proximal the heel portion to dismount from the shoe.

18. The interface of claim 17, wherein the shoe further comprises at least one elastic spring energy storage element disposed on the base proximal the heel portion,
wherein the at least one elastic spring energy storing element stores elastic spring energy when elastically deformed into a first position co-planar with the base when the reusable optical sensor is removably mounted in the shoe, and
wherein the at least one elastic spring energy storage element transfers elastic energy stored therein to the reusable optical sensor when the at least one elastic spring energy storage element springs to a second position angled away from the plane of the base and toward the reusable optical sensor, pushing the reusable optical sensor to be dismounted from the shoe.

19. The interface of claim 17, wherein the compliant structure comprises a material selected from the group consisting of open celled foam, closed cell foam, natural rubber, synthetic rubber, black polyurethane foam, and thermoplastic elastomer.

20. The interface of claim 17, wherein the compliant structure conforms to a part of patient's body selected from the group consisting of a deltoid, an upper arm, a calf, a thigh, a forearm, an upper back, and a lower back.

21. The interface of claim 17, wherein the shoe further comprises an opening passing completely through the base proximal the medial portion of the shoe, wherein the opening comprises a perimeter that is adapted to frame optical elements proud from the reusable optical sensor.

22. The interface of claim 21, further comprising an optically clear window aligned with the opening.

23. The interface of claim 17, further comprising a removable liner, wherein at least a portion of the removable liner is sufficiently opaque to prevent a user from using the reusable optical sensor without first removing the removable liner.

24. The interface of claim 17, wherein the reusable optical sensor comprises a security sensor which prevents the reusable optical sensor from operating when the reusable optical sensor is not removably mounted in the shoe.

25. The interface of claim 24, wherein the security sensor comprises a hall sensor and the shoe comprises a magnet coupled to the base, wherein the magnet generates a magnetic field that can only be detected by the hall sensor of the reusable optical sensor when the reusable optical sensor is removably mounted in the shoe.

26. The interface of claim 17, wherein the barrier is opaque.

27. The interface of claim 17, wherein the barrier has a minimal height dimension that is equal to or greater than a minimum thickness dimension of the reusable optical sensor.

28. The interface of claim 17, wherein the reusable optical sensor comprises at least a portion that receives a magnet coupled to the base.

29. A method of removably mounting a reusable optical sensor in a disposable patient interface, comprising:
providing the reusable optical sensor comprising a first end proximal a cable or case extension of the sensor and a second end opposite the first end;
providing a patient interface comprising:
a conformal placement element that has a compliant structure which conforms to a patient's body upon placement thereon,
a shoe fixed with the conformal placement element and which removably receives the reusable optical sensor, the shoe comprising a heel portion, a toe portion, a medial portion therebetween, a base positioned against a second surface of the conformal placement element from the heel portion to the toe portion, and a barrier extending around a perimeter of the base, the barrier comprising a first wall portion and a second wall portion opposite to the first wall portion, the first wall portion and the second wall portion each comprising at least one aperture which removably locks with at least one protrusion on the reusable optical sensor, and
at least one actuator projecting from the barrier proximal the heel portion; sliding the second end of the sensor toward the barrier proximal the toe portion of the shoe so that at least one protrusion proximal the second end of the reusable optical sensor removably locks with at least one aperture proximal the toe portion of the shoe; and pushing the first end of the reusable optical sensor toward the base proximal the heel portion of the shoe so that at least one protrusion proximal the first end of the reusable optical sensor removably locks with the at least one aperture proximal the heel portion of the shoe, thereby removably mounting the reusable optical sensor in the disposable patient interface;

wherein dismounting the reusable optical sensor comprises:

pressing the at least one actuator to cause a flexing motion of the shoe, which in turn causes the at least one protrusion proximal either the first wall portion or the second wall portion to unlock from the at least one aperture removably locked with the at least one protrusion proximal either the first wall portion or the second wall portion, which in turn causes at least a portion of the reusable optical sensor proximal the heel portion to dismount from the shoe; and optionally lifting a cable or end of a case extension disposed proximal the first end of the sensor away from the shoe, wherein the pressing and lifting are optionally performed using a same hand of the user, thereby dismounting the sensor from the patient interface.

* * * * *